United States Patent [19]

Payne

[11] Patent Number: 5,006,336

[45] Date of Patent: Apr. 9, 1991

[54] NOVEL COLEOPTERAN-ACTIVE BACILLUS THURINGIENSIS ISOLATE

[75] Inventor: Jewel Payne, San Diego, Calif.

[73] Assignee: Mycogen Corporation, San Diego, Calif.

[21] Appl. No.: 205,122

[22] Filed: Jun. 10, 1988

[51] Int. Cl.[5] ........................ C12N 1/20; A01N 63/00

[52] U.S. Cl. .................................. 424/93; 435/252.5; 435/822; 530/350

[58] Field of Search ............... 424/93; 435/252.5, 822; 530/350

[56] References Cited

U.S. PATENT DOCUMENTS

| | | | |
|---|---|---|---|
| 3,150,062 | 9/1964 | Greenberg et al. | 424/93 |
| 3,946,107 | 3/1976 | Westall | 424/93 |
| 4,467,036 | 8/1984 | Schnepf et al. | 435/849 X |
| 4,695,455 | 9/1987 | Barnes et al. | 424/93 |
| 4,764,372 | 8/1988 | Herrnstadt et al. | 424/93 |
| 4,766,203 | 8/1988 | Krieg et al. | 530/370 |
| 4,771,131 | 9/1988 | Herrnstadt et al. | 424/93 |
| 4,797,276 | 1/1989 | Herrnstadt et al. | 424/93 |

FOREIGN PATENT DOCUMENTS 0202739 11/1986 European Pat. Off. .

OTHER PUBLICATIONS

J. Appl. Ent. 104 (1987), 417–424, Krieg et al.
Biol. Abstr 77(8)=6409, 58279, Cantwell et al. (1984).
Biol. Abstr. 79(3)=AB-260, 20689, Cantwell et al. (1985).
Chem. Abstr. 89, 158714h, Galani et al. (1978).

*Primary Examiner*—Howard E. Schain
*Attorney, Agent, or Firm*—Saliwanchik & Saliwanchik

[57] ABSTRACT

The subject invention concerns a novel and useful insecticide with activity against insect pests of the order Coleopters. Pests in the order Coleoptera do heavy damage to crops, e.g., corn and potatoes. The insecticide of the subject invention is a novel *B. thuringiensis* microbe referred to as *B.t.* PS122D3, or mutants thereof. The spores or crystals of this microbe are useful to control coleopteran pests in various environments.

11 Claims, 2 Drawing Sheets

B.t.s.d. PS122D3

CORNSTEEP
MEDIUM

B.t.s.d. PS122D3

FISHMEAL
MEDIUM

A    B

A. B.t. PS122D3

B. B.t.sd.

NOVEL COLEOPTERAN-ACTIVE BACILLUS THURINGIENSIS ISOLATE

BACKGROUND OF THE INVENTION

Bacillus thuringiensis (B.t.) produces an insect toxin designated as δ-endotoxin. It is synthesized by the B.t. sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of B.t. covers insect species within the order Lepidoptera, many of which are major pests in agriculture and forestry. The activity spectrum also includes the insect order Diptera, which includes mosquitos and black flies. See Couch, T.L. (1980) "Mosquito Pathogenicity of *Bacillus thuringiensis* var. *israelensis*," Developments in Industrial Microbiology 22:61–76; Beegle, C. C., (1978) "Use of Entomogenous Bacteria in Agroecosystems," Developments in Industrial Microbiology 20:97–104. Krieg, et al., Z. ang. Ent. (1983) 96:500–508, describe a B.t. isolate named *Bacillus thuringiensis* var. *tenebrionis*, which is reportedly active against two beetles in the order Coleoptera. These are the - Colorado potato beetle, *Leptinotarsa decemlineata*, and *Agelastica alni*.

In European Patent Application 0 202 739 there is disclosed a novel B.t. isolate active against Coleoptera. It is known as *B. thuringiensis* var. *san diego* (B.t.sd.).

Coleopteran-active strains, such as B.t.sd., can be used to control foliar-feeding beetles. The Colorado potato beetle (*Leptinotarsa decemlineata*), for example, is susceptible to the delta-endotoxin of B.t.sd. and larvae are killed upon ingesting a sufficient dose of spore/crystal preparation on treated foliage.

A number of crops are attacked by flea beetles. These beetles belong to the family Chrysomelidae, the *decemlineata*. The adults can cause extensive damage by feeding on the foliage.

BRIEF SUMMARY OF THE INVENTION

The subject invention concerns a novel *Bacillus thuringiensis* (B.t.) isolate which has activity against coleopteran pests. For example, the novel B.t. isolate, known herein as *Bacillus thuringiensis* PS122D3 (B.t. PS122D3), has thus far been shown to be active against the Colorado potato beetle (*Leptinotarsa decemlineata*). More extensive host range studies are in progress.

The subject invention also includes mutants of B.t. PS122D3 which have substantially the same pesticidal properties as B.t. PS122D3. Procedures for making mutants are well known in the microbiological art. Ultraviolet light and nitrosoguanidine are used extensively toward this end.

Further, the invention also includes the treatment of substantially intact B.t. PS122D3 cells to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated B.t. PS122D3 cell acts as a protective coating for the pesticidal toxin. The toxin becomes available to act as such upon ingestion by a target insect.

DETAILED DISCLOSURE OF THE INVENTION

The novel *Bacillus thuringiensis* isolate of the subject invention has the following characteristics:

Characteristics of B.t. PS122D3

Colony morphology—Large colony, dull surface, typical B.t.

Vegetative cell morphology—typical B.t.

Culture methods—typical for B.t.

Flagellar serotyping—PS122D3 belongs to serovar morrisoni.

Inclusions—square wafer.

Plasmid preparatons—agarose gel electrophoresis of plasmid preparations distinguishes B.t. PS122D3 from B.t.sd. and other B.t. isolates.

Alkali-soluble proteins—SDS polyacrylamide gels show 64 and 72 kilodalton proteins.

Coleopteran toxin—Bioassay shows activity against Colorado potato beetle with an $LC_{50}$ of 2.4 μg protein/ml suspension.

A comparison of the characteristics of the well-known B.t. strain *B. thuringiensis* var. *San diego* (B.t.sd.) with *B. thuringiensis* PS122D3 (B.t. PS122D3) shows that PS122D3 has an $LC_{50}$ of 2.4 μg protein/ml suspension, as compared to 2.7 μg protein/ml suspension for B.t.sd.. This comparison was made on a standard leaf-dip bioassay against Colorado potato beetle (CPB), described infra.

Figure 1:
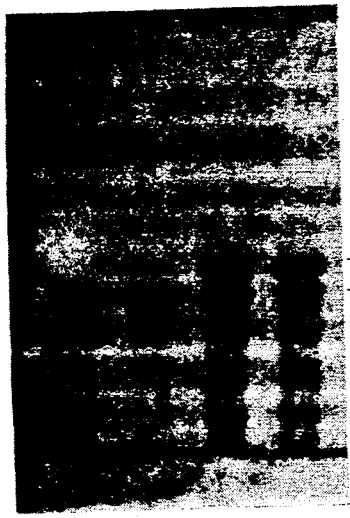
FIG. 1: A Photograph of a Standard SDS Polyacrylamide Gel of B.t.sd. and B.t. PS122D3
Figure 1:
Figure 2:
FIG. 2: A Photograph of Plasmid Preparations from B.t.sd. and B.t. PS122D3 Plasmids were cut with Hind III and run on a 0.8% Tris-acetate agarose gel.

The culture disclosed in this application has been deposited in the Agricultural Research Service Patent Culture Collection (NRRL), Northern Regional Research Center, 1815 North University Street, Peoria, Ill. 61604, USA.

| Culture | Repository No. | Deposit date |
|---|---|---|
| Bacillus thuringiensis PS122D3 | NRRL B-18376 | June 9, 1988 |

The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for th.e enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

B.t. PS 122D3, NRRL B-18376, can be cultured using standard art media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

Formulated products can be sprayed or applied onto foliage to control phytophagous beetles or caterpillars.

Another approach that can be taken is to incorporate the spores and crystals of B.t. PS122D3 into bait granules containing an attractant and applying these granules to the soil for control of soil-inhabiting Coleoptera. Formulated B.t. PS122D3 can also be applied as a seed-coating or root treatment or total plant treatment.

The B.t. PS122D3 cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., Animal Tissue Techniques, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

Following are examples which illustrate procedures, including the best mode, for practicing the invention. These examples should not be construed as limiting. All percentages are by weight and all solvent mixture proportions are by volume unless otherwise noted.

EXAMPLE 1—CULTURING B.T. PS122D3, NRRL B-18376

A subculture of B.t. PS122D3, NRRL B-18376 can be used to inoculate the following medium, a peptone, glucose, salts medium.

| | |
|---|---|
| Bacto Peptone | 7.5 g/l |

-continued

| | |
|---|---|
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$ · 7H$_2$O | 2.46 g |
| MnSO$_4$ · H$_2$O | 0.04 g |
| ZnSO$_4$ · 7H$_2$O | 0.28 g |
| FeSO$_4$ · 7H$_2$O | 0.40 g |
| CaCl$_2$ Solution (100 ml) | |
| CaCl$_2$ · 2H$_2$O | 3.66 g |
| pH 7.2 | |

The salts solution and CaCl$_2$ solution are filtersterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2—TESTING OF B.T. PS122D3, NRRL B-18376 SPORES AND CRYSTALS

B.t. PS122D3, NRRL B-18376 spores and crystals were tested against the Colorado potato beetle (CPB). B.t. PS122D3 has an LC$_{50}$ of 2.4 µg protein/ml in the CPB assay. The assay for the Colorado potato beetle was conducted as follows:

CPB Bioassay—Early second instar larvae of Leptinotarsa decemlineata are placed on potato leaves which have been dipped in suspensions containing Bacillus thuringiensis preparations. The larvae are incubated at 25° C. for 4 days, and larval mortality is recorded and analyzed using probit analysis.

EXAMPLE 3—COMPARISON OF TOXIN PRODUCTION IN B.T. PS122D3 AND B.T.SD.

| Cottonseed medium | Total Toxin (mcg/ml) |
|---|---|
| B.t.sd. | 901 |
| B.t. PS122D3 | 1584 |
| Fishmeal medium | |
| B.t.sd. | 1043 |
| B.t. PS122D3 | 1777 |

The composition of the above media is as follows:

| Cottonseed medium | g/liter |
|---|---|
| Cottonseed flour | 15 |
| Cornsteep solids | 15 |
| Glucose | 20 |
| Peptone | 2 |
| Yeast extract | 2 |
| CaCO$_3$ | 1 |
| Adjust pH to 6.8 | |
| Sterilize glucose separately | |

| Fishmeal medium | g/liter |
|---|---|
| Fishmeal | 30 |
| Maltodextrin | 10 |
| Glucose | 10 |
| Yeast extract | 2 |
| CaCO$_3$ | 1 |
| Adjust pH to 6.8 | |
| Sterilize glucose separately | |

The fermentation conditions given in Example 1 can be used.

The results obtained in this example show that PS122D3 produces a significantly larger amount of toxin than does *B.t.sd.*. Preliminary data from 1988 small plot field trials on potatoes indicate that a 10% aqueous formulation of PS122D3 has higher levels of activity against the CPB than a comparable formulation of *B.t.sd.*. In these trials, formulation rates of 2 quarts and 3 quarts per acre of PS122D3 resulted in significantly higher levels of potato plant protection than rates of 3 quarts to 8 quarts per acre of formulated *B.t.sd.*

The above, along with differences in the plasmids, clearly distinguishes these two *B.t.* coleopteran-active isolates.

We claim:

1. A process for controlling coleopteran insect pests with a δ-endotoxin which comprises contacting said insect pests with an insect-controlling effective amount of *B. thuringiensis* PS122D3 having the identifying characteristics of NRRL B18376, or mutants thereof.

2. A process, according to claim 1, wherein said insect pest is the Colorado potato beetle.

3. A process, according to claim 1, wherein said insect pest is contacted with an insect-controlling sufficient amount of *B. thuringiensis* PS122D3, by incorporating said *B. thuringiensis* PS122D3 into a bait granule and placing said granule on or in the soil when planting seed of a plant upon which plant insect pest is known to feed.

4. A process for controlling soil-inhabiting insect pests of the order Coleoptera with a δ-endotoxin which comprises
   (1) preparing a bait granule comprising *B. thuringiensis* PS122D3, or mutants thereof, spores or crystals; and
   (2) placing said bait granule on or in the soil.

5. A process, according to claim 5, wherein said bait granule is applied at the same time corn seed is planted in the soil.

6. A process, according to claims 1 or 4, wherein substantially intact *B.t.* PS122D3 cells, or mutants thereof, are treated to prolong the pesticidal activity when the substantially intact cells are applied to the environment of a target pest.

7. A composition of matter comprising *B. thuringiensis* PS122D3, or mutants thereof, spores or crystals in association with an insecticide carrier.

8. A composition of matter, according to claim 7, wherein said carrier comprises beetle phagostimulants or attractants.

9. A composition of matter comprising *B. thuringiensis* PS122D3, or mutants thereof, in association with formulation ingredients applied as a seed coating.

10. A biologically pure of culture of *Bacillus thuringiensis* PS122D3, having the identifying characteristics of NRRL B-18376, or mutants, thereof, having activity against insect pests of the order Coleoptera.

11. A process, according to claim 1, wherein the coleopteran pests are present on stored products.

* * * * *

UNITED STATES PATENT AND TRADEMARK OFFICE
CERTIFICATE OF CORRECTION

PATENT NO.    :   5,006,336

DATED         :   April 9, 1991

INVENTOR(S)   :   Jewel Payne

It is certified that error appears in the above-identified patent and that said Letters Patent is hereby corrected as shown below:

On the title page:
Abstract    line 3:     "Coleopters" should read --Coleoptera--.

Column 1    line 36:    Delete spaces after "is" and before "susceptible".

Column 6    line 11:    "claim 1" should read --claim 2--.

Column 2    line 37:    "PS122D3" should read --PS122D3.--.

Column 3    line 12:    "  5 completion" should read --completion--.

Signed and Sealed this

Fifth Day of January, 1993

*Attest:*

DOUGLAS B. COMER

*Attesting Officer*    Acting Commissioner of Patents and Trademarks